United States Patent [19]

Zitowitz et al.

[11] 4,016,291

[45] Apr. 5, 1977

[54] BENZENESULFONYL UREA COMPOUNDS AND THEIR THERAPEUTIC USE

[75] Inventors: Lester Zitowitz, West Orange; Lewis A. Walter, Madison; Arnold J. Wohl, North Caldwell, all of N.J.

[73] Assignee: Schering Corporation, Kenilworth, N.J.

[22] Filed: Mar. 15, 1976

[21] Appl. No.: 667,243

Related U.S. Application Data

[60] Division of Ser. No. 529,888, Dec. 5, 1974, which is a continuation-in-part of Ser. No. 165,588, July 23, 1971, abandoned, which is a continuation-in-part of Ser. No. 877,000, Nov. 14, 1969, abandoned, which is a continuation-in-part of Ser. No. 853,504, Aug. 27, 1969, abandoned.

[52] U.S. Cl. .............................. 424/322; 260/553 D
[51] Int. Cl.$^2$ ...................................... C07C 127/16
[58] Field of Search ............... 424/322; 260/553 D

[56] References Cited

UNITED STATES PATENTS 3,097,241   7/1963   Kroger et al. ................. 260/553 D

OTHER PUBLICATIONS

Holland, J. Org. Chem. vol. 26, pp. 1662–1665 (1961).

Primary Examiner—Gerald A. Schwartz
Attorney, Agent, or Firm—Stephen B. Coan; Raymond A. McDonald

[57] ABSTRACT

This application is directed to novel sulfonyl urea compounds, their non-toxic pharmaceutically acceptable salts, and to processes for making and using said compound. Exemplary of the sulfonyl ureas of this invention is N-(aralkyl)-N'-(p-benzenesulfonyl)urea.

8 Claims, No Drawings

BENZENESULFONYL UREA COMPOUNDS AND THEIR THERAPEUTIC USE

This application is a division of our-co-pending application Ser. No. 529,888 which in turn is a continuation-in-part application of our copending application Ser. No. 165,588, filed July 23, 1971 (now abandoned), which application in turn, is a continuation-in-part application of application Ser. No. 877,000, filed Nov. 14, 1969 (now abandoned), which application in turn, is a continuation-in-part application of application Ser. No. 853,504, filed Aug. 27, 1969 (now abandoned).

This invention relates to compositions of matter classified in the art of chemistry as N(aralkyl)-N'-benzenesulfonyl ureas and the pharmaceutically acceptable salts thereof.

The invention sought to be patented in one of its process aspects resides in the condensation reaction of an N-(benzenesulfonyl) carbamic acid ester, or a functional equivalent thereof, with an aralkylamine to obtain a desired product of this invention.

In another of its process aspects this invention resides in the method of treating a living animal for cardiac arrhythmia by administering a therapeutically effective quantity of a composition of this invention.

In another of its process aspects this invention resides in the method of eliciting an anti-anginal effect in a living mammalian body by administering a therapeutically effective quantity of a composition of this invention.

Still another process aspect of this invention resides in the method for the prevention of the loss of glutamic oxalotransaminase activity in cardiac tissue of mammals.

More specifically, the tangible embodiments of the compositions of matter of this invention are those chemical compounds having the structural formula:

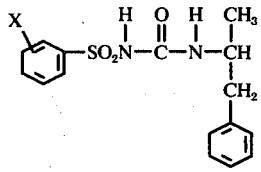

and their salts thereof formed with pharmaceutically acceptable bases, wherein X is methyl.

In those instances wherein the phenyl ring is substituted with methyl, such substituent may be located in the ortho or meta positions but it is most preferred to have the substituent in the para position of the phenyl ring as well as to have mono substituted phenyl moieties. Typical bases which may be used to form pharmaceutically acceptable salts are those well known in the art, especially those such as the alkali and alkaline earth metal hydroxides and oxides and ammonium.

In general, the compounds of this invention (I) may be prepared by reacting an appropriately X substituted phenylsulfonyl carbamic acid ester, or a functional equivalent thereof, with equivalent or slightly excess quantities of the appropriate phenethyl or phenylpropyl amine according to analogous techniques described in the prior art, (J. Org. Chem. 23, 927, 1958). It is advantageous to effect the condensation by heating the reactants together within the temperature range of about 90–180° C, preferably at about reflux temperatures, said reaction preferably being conducted in the presence of an inert solvent such as benzene, toluene, xylene, dimethylformamide, acetonitrile, and the like. After condensation, the solvent is removed by distillation or filtration, the residue dissolved in a suitable solvent, e.g. hot alcohol, ether, and the like. Purification is then effected by standard techniques, and, if desired, the product is converted to its alkali metal, alkaline earth metal or ammonium salt by standard salification techniques. The foregoing condensation reaction may be depicted as follows:

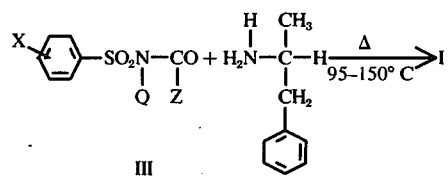

III wherein X is as previously defined, with Q being hydrogen, Z being alkoxy or Z and Q together signify a double bond between the carbon and nitrogen atoms. When Q and Z form a double bond the compounds of II are isocyanates, otherwise they are alkyl esters of the benzenesulfonyl carbamic acids.

Alternatively, the foregoing condensation reactions may also be effected by melting the reactants together without the use of a solvent.

Additionally, the alkali metal salt of an appropriate sulfonamide may be condensed with the appropriate urea (V) by heating such reactants together, or else an appropriate sulfonamide may be condensed with isocyanate according to the following depicted reaction schemes:

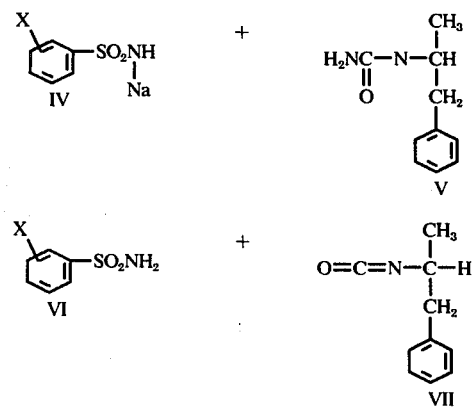

wherein X is as previously defined.

In their application for their functional use characteristics the compounds of this invention are preferably used in their levorotatory form, although either the dextrorotatory form or racemate may be used. In practice, it is preferred to prepare the optically active compounds by the employment of the optically active reactant (e.g. d-amphetamine) in the condensation. However, in those instances wherein a racemic mixture is obtained, the mixture is readily resolved by standard techniques.

The following examples typify the preferred methods of synthesis of the compounds of this invention.

EXAMPLE 1

1-(d-α-Methyl phenethyl)-3-(p-tolylsulfonyl) urea

Five grams of d-amphetamine in 35 ml. of toluene is added slowly with stirring to 7.5 g. of ethyl N-p-toluenesulfonyl carbamate in 75 ml. of toluene. The mixture is refluxed for 3 hours, the solvent removed in vacuo and the residue is dissolved in hot alcohol. The hot alcohol solution is poured with good stirring into 10 ml. of 5% hydrochloric acid and the product is filtered, washed with water and crystallized from acetone to yield 1-(d-α-methyl phenethyl)-3-(p-tolylsulfonyl) urea, m.p. 180°–181° C $[\alpha]_D^{26}$ −33° C=2% dioxane.

EXAMPLE 2

1-(d-α-Methyl phenethyl)-3-(p-tolylsulfonyl) urea

To a solution of 7 g. of d-amphetamine in 200 ml. of toluene, add dropwise, with stirring, a solution of 9.8 g. of p-methylphenylsulfonyl isocyanate in 75 ml. of toluene. Heat on a steam bath for 30 minutes, cool and filter off the residue, water wash and crystallize from acetone to obtain 1-(d-α-methyl phenethyl)-3-(p-tolylsulfonyl) urea, m.p. 180°–181° C $[\alpha]_D^{26}$ −33° C=2% dioxane.

EXAMPLE 3 d-1-Methyl-1-(α-methyl phenethyl)-3-(p-tolylsulfonyl)urea

A solution of 80 g. of d-desoxyehedrine in 1 liter or dry benzene is chilled to 10° C and 56 g. of p-toluenesulfonylisocyanate in 200 ml. of dry benzene is added with good stirring for 15 minutes. The temperature of the mixture rises to about 30° and stirring is continued without cooling until it falls to room temperature. The mixture is heated at 65°–70° C for 2 hours, cooled to 10° C and extracted successively with 350 ml. of cold 5% hydrochloric acid, 50 ml. of the same solution, 50 ml. of water and 20 ml. of 5% sodium bicarbonate. The benzene is evaporated in vacuo and the slightly gummy residue is crystallized from 100 ml. of acetonitrile. The yield of white crystalline product of this example, m.p. 145°–149° $[\alpha]_D^{26}$ +13.2° C=2% in ethanol is 70 g.

As is apparent to one skilled in the art, by substituting the amphetamine and the carbamate or isocyanate reactants of the foregoing examples with appropriate reactants, and by substantially following the procedures outlined in those examples, the other compounds of this invention may also be produced.

1-(α-methyl phenethyl)-3-(m-tolylsulfonyl) urea, m.p. 147°–149° C $[\alpha]_D^{26}$ 3.9° C=2% dioxane, 1-(α-methyl phenethyl)-3-(p-tolylsulfonyl) urea, m.p. 158°–159.5° C (racemate), and 1-(60 -methyl phenylpropyl)-3-(p-tolylsulfonyl) urea, m.p. 155°–156.5° C (racemate).

Although the above-described procedures are representative of the preferred modes of preparation for the compounds of this invention, other procedures are also available. Such procedures may be represented by the following outlined procedures for the preparation of 1-(α-methyl phenethyl)-3-(p-tolylsulfonyl) urea, it being noted that the below described procedures, with a few rather obvious exceptions, are available for the preparation of compounds of formula I other than the specifically mentioned compound. Particularly useful of the alternative procedures is the hydrogenolysis process wherein certain key intermediates are subjected to catalytic hydrogenation, preferably using palladium on charcoal, although the usual and standard techniques may be applied. The hydrogenolysis technique is particularly effective when either or both nitrogen actions are substituted such as those benzenesulfonyl ureas bearing benzyl radicals on the nitrogen atom(s), although other radicals (e.g. —COOCH₂O, and —OCH₂O) may similarly be employed.

Similarly, hydrogenolysis by catalytic hydrogenation is effective in removing hydroxyl groups from the amine moiety containes in the compounds of formula I, or to effect a deoxygenation of a ketoamine derivative of the compounds of formula I. Similarly, dehalogenation of compounds bearing halogeno radicals in either or both of the phenyl ring moieties may be effected by standard catalytic hydrogenation. Still another effective catalytic hydrogenation process is that applied in order to cleave either a cyclopropylamine to form the desired α-methyl phenethyl moiety or to cleave an aziridine moiety to again produce the desired α-methyl phenethyl moiety of the compounds of this invention. Thus to produce the 1-(α-methyl phenethyl)-3-(p-tolylsulfonyl) urea by hydrogenolysis the following depicted intermediates (or their functional equivalents) may be employed:

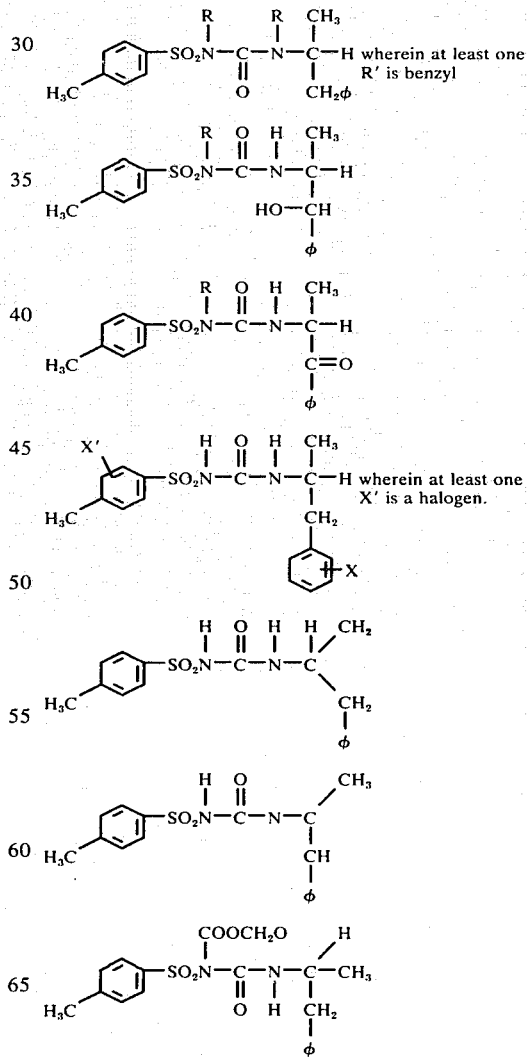

-continued

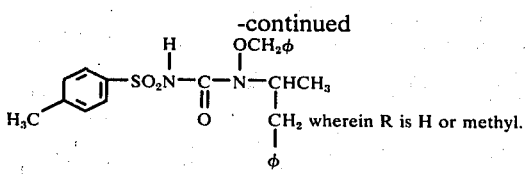

wherein R is H or methyl.

Another approach to synthesize the compounds of this invention is the oxidation of appropriate sulfinimides or sulfeneimides in order to convert the sulfur atom to its proper oxidative state for the sulfonyl ureas of this invention. One convenient method is the treatment of the sulfinimide with hydrogen peroxide.

Still other approaches useful in the obtention of compounds of this invention are the removal of certain groups by such standard and well-known techniques as (a) the hydrolysis of the appropriate guanadino compounds, (b) the removal of a diazonium salt moiety with treatment hypophosphorous acid, (c) by removal of a mercapto moiety by treatment with zinc in the presence of acetic acid, (d) by hydrolysis of an iminolether, as well as by other well known standard techniques.

Still another technique is by replacement reactions such as by the replacement of the sulfur atom of an appropriate thiourea with oxygen by reaction with mercuric oxide.

Having described the methods for preparing the compounds of this invention the manner of using the invention sought to be patented in its process aspect will not be described.

As stated above, the method of treating a living mammal for cardiac arrhythmias is effected by administering a therapeutically effective quantity of a 1-($\alpha$-alkyl aryl)-3-(benzenesulfonyl) urea of this invention (formula I). The therapeutically effective quantity of a compound may be ascertained by standard and well-known techniques in the art. One such laboratory technique is the digitalis-induced arrhythmia assay in the dog wherein mongrel dogs of either sex are anesthetized with 35 mg./kg. of pentobarbital sodium, i.v. A fermoral vein and artery are cannulated for drug infusions and recording of systemic pressure, respectively. The dog also is prepared to record limb lead II electrocardiograms.

After a period of stabilization in which the systemic blood pressure and electrocardiogram are followed, a dose of 35 ug./kg. of digitalis is given, i.v. If no conduction abnormality occurs in the form of nodal or ventricular arrhythmias, a second dose of 35 ug./kg. of digitalis is given. This dose of digitalis is given every 15 minutes until an arrhythmia develops and lasts at least 30 minutes. The experimental drug is then given, i.v., in an attempt to normalize the abnormal EGG. Quinidine or propanolol are used as reference standards.

From this assay, as well as other assay techniques, (e.g. electrically induced fibrillation) it is determined that the compounds of this invention elicit an anti-arrhythmic effect in mammals at from 2 to 50 mg./kg. of body weight. It is also found that the compounds of this invention are especially useful in the prevention and reversal of ventricular arrhythmias. Particularly useful as an anti-arrhythemic agent is the compound 1-($\alpha$-methyl phenethyl)-3-(tolylsulfonyl) urea which is found to be especially useful in the treatment of supraventricular arrhythmia. As can be seen from the results shown in the Chart I, this compound is particularly effective at a dosage level of 5 mg./kg. of body weight. Another particularly effective compound is 1-(methyl)-1-($\alpha$-methyl phenethyl)-3-(tolylsulfonyl) urea.

Chart I

SUMMARY OF ANTI-ARRHYTHMIA ACTIVITY OF 1-($\alpha$-METHYL PHENETHYL) 3-(TOLYLSULFONYL) UREA AND PROPANOL IN DIGITALIS TOXICITY

| Treatment, i.v.* | % Abnormal Beats | Duration of Response |
|---|---|---|
| Control | 80–95 | 30 min. |
| Experimental Drugs | | |
| 1 mg./kg. | No changes | — |
| 2 mg./kg. | 50 | 60 min. |
| 5 mg./kg. | 10 | 120 min. |
| 10 mg./kg. | 70 | 60 min. |
| Propanol | | |
| 1 mg./kg. | 50 | 30 min. |
| 2 mg./kg. | 50 | 30 min. |

*Each dose tested at least three times. Seven dogs were used for the study.

The method for the prevention of the symptoms of angina pectoris (i.e. severe sub-sternal pain, dyspnea, and hypoxic changes in limb-lead electrocardiogram, e.g. depression of the S–T segment, as well as other well-known factors associated with angina pectoris) is effected by administering a therapeutically effective quantity of a 1-($\alpha$-alkyl aryl)-3-(benzenesulfonyl) urea of this invention. The therapeutically effective dose for the treatment of angina pectoris is determined by modified Rona and Stanton procedures for producing cardiac necrosis, in rats, as follows:

Male Charles River rats, not less than 200 gms. are used exclusively. The animals are conditioned at least one week before any drug is given. Animals of comparable age and body weights are separated into control and experimental groups and allowed standard lab chow and water ad libitum. The provoking drug is 80 mg./kg. of di-isoproterenol HCl (ISU) injected subcutaneously once per day for 2 days. The control groups receives an isovolumic injection of physiological saline by the same route. The experimental group receives an appropriate dose of test compound intraperitoneally or orally 2 days prior to the start of ISU injection. ISU is started on the third day of the drug regimen, and both agents are given to their respective groups for the following 2 days. The experimental drug is given as two equally divided doses each day; on days three and four it is given 30 minutes before and 30 minutes after ISU. A fourth group of rats received ISU, s.c., plus 250 ug./kg. of nitroglycerine as a drop of solution on the oral mucous membranes 5, 30, 60 and 90 minutes after the ISU challenge. The nitroglycerin group determines the sinsitivity of any given litter of rats to this standard anti-angina agent. The initial and final body weights of all animals are recorded, and then they are sacrificed 24 hours after the second ISU injection. The heart of each animal is removed, blotted dry, weighed and graded for degree of necrosis. Four areas of the heart are examined for lesions, the apex, interventricular septum, left ventricle, and right ventricle. A 0–4 grading system is used as follows:

0 = no lesions
1 = mottling of apex and distal left ventricle
2 = well demarcated necrotic areas on apex
3 = large infarct-like necrosis in the left ventricle extending to the intraventricular septum.
4 = large infarct-like necrosis involving both ventricles and the intraventricular septum.

Scoring may also be made at 0.5, 1.5, 2.5 and 3.5 degrees of severity. An average necrosis score for each group is determined and a percent protection is calculated.

Following the collection of these data an evaluation is completed by the use of modern day statistical analysis techniques. Using these techniques of program has been designed which computes the percentage of heart weight to body weight, and the mean, variance, standard deviation and standard error of these percentages. One-way analysis of variance is performed on intergroup scores of necrosis for statistical evaluation.

From this assay, as well as by comparison with other prior art compounds useful in the treatment of angina pectoris, the compounds of this invention exert their antianginal effect within the dosage range of about 10 to 50 mg./kg. of body weight with 20 mg. being the preferred oral dosage.

Similarly, the dosage range for the prevention of the loss of glutamic oxalotransaminase enzyme activity in cardiac tissue is measured by well-known techniques and assay procedures. From these procedures it is determined that the compounds of this invention are effective in the range of about 10 to 40 mg./kg. of body weight, (orally) with 20 mg./kg. being preferred.

Of course, the ultimate dosage of the compounds of this invention will depend upon the severity, the stage and the individual characteristics of each case and will be finally determined by the attending diagnostician by the use of standard and recognized parameters for this purpose.

From the results of the assay techniques for the determination of (a) antiarrhythmic activity, (b) antianginal activity and (c) prevention of the loss of glutamic oxalotransaminase enzyme activity in cardiac tissue, 1-($\alpha$-methyl phenethyl-3-(tolylsulfonyl) urea is a particularly effective and desirable compound for treatment of mammals for these conditions. Indeed, this compound demonstrates such a significantly superior therapeutic index and such superior usecharacteristics relative to the other members of the compounds of formula I, that adequate reason exists for its separate classification. Also, when its applied use characteristics are measured against those prior art compounds previously known to be useful for the indications herein set forth, it is quite apparent that 1-($\alpha$-methyl phenethyl)-3-(tolylsulfonyl) urea is indeed a uniquely useful therapeutic agent. It is also to be noted that the levorotatory form of this compound is superior to either the dextro or racemic mixture of that compound. Thus, of the compounds of this invention 1-(d-$\alpha$-methyl phenethyl)-3-(tolylsulfonyl) urea (i.e. the compound produces by example 1) is especially desirable for the therapeutic indications herein set forth. Another compound found to be particularly potent and useful for the aforementioned therapeutic effects is 1-methyl-1-(2-phenylpropyl)-3-(p-tolylsulfonyl)-urea.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms, as for example, tablets, capsules and suppositories, or in liquid forms as for example, elixirs, emulsions and injectables. In the formulation of pharmaceutical preparations there can be employed such substances which do not react with the active substance as for example, water, gelatin, lactose, starches, magnesium stearate, calcuim carbonate, talc, vegetable oils, benzyl alcohols, gums, polyalkylene glycols, petroleum jelly and the like. The active ingredient of such pharmaceutical preparations is preferably present in the preparation in such proportions by weight that the proportion by weight in the active ingredient to be administered lies between 0.1 and 50%.

Tablet Formulation

The following formulation provides for the manufacture of 1,000 tablets:

|     |                                                  | Grams |
| --- | ------------------------------------------------ | ----- |
| (1) | 1-(d-$\alpha$-Methyl phenethyl)-3-(p-tolylsulfonyl) urea | 25    |
| (2) | Lactose, U.S.P.                                  | 181   |
| (3) | Corn Starch, U.S.P.                              | 92.5  |
| (4) | Magnesium Stearate                               | 1.5   |

Thoroughly granulate a mixture of 92.5 g. of corn starch and the lactose with a paste prepared by dissolving 20 gms. of corn starch in 100 ml. of hot distilled water. Dry the resulting granulation at 40°–45° C and pass it through a No. 16 mesh screen. To the dried, screened granulation add a blended mixture of the active ingredient (1) and the magnesium stearate. Thoroughly blend and then press into tablets of 500 mg. each.

Capsule Formulation

The following formulation provides for the manufacture of 1,000 capsules:

|     |                                                  | Grams |
| --- | ------------------------------------------------ | ----- |
| (1) | 1-(d-$\alpha$-Methyl phenethyl)-3-(p-tolylsulfonyl) urea | 25    |
| (2) | Lactose                                          | 273.5 |
| (3) | Magnesium stearate                               | 1.5   |

Mix active ingredient (1) with the lactose and blend in the magnesium stearate. Fill hard gelatin capsules with 300 mg. each of the blended mixture to produce capsules containing 25 mg. of 1-(d-$\alpha$-methyl phenethyl)-3-(p-tolylsulfonyl) urea.

Parenteral Formulation

The following formulation provides for the manufacture of 1,000 vials each containing 10 mg. of active ingredient:

|     |                                                       | Grams |
| --- | ----------------------------------------------------- | ----- |
| (1) | 1-(d-$\alpha$-Methyl phenethyl)-3-(p-tolylsulfonyl) urea | 10.0  |
| (2) | Monobasic potassium phosphate                         | 6.0   |
| (3) | Water for injection, U.S.P.   q.s.   liter            | 1.0   |

Dissolve ingredients (1), (2), and (3) in approximately 80 percent of the volume of water and filter the resulting solution. Add to the filtrate sufficient water to make to a 1000 ml. volume. Sterile-filter the solution and asceptically fill one milliliter portions of the so-prepared solution into two milliliter vials, then lyophylize.

After the lyophilized cake is dry, asceptically stopper the vials with rubber plugs and seal.

We claim:

1. A method for the prevention and reversal of the symptoms of angina pectoris which comprises administering a therapeutically effective quantity of a compound of the formula

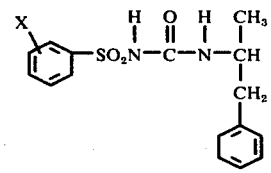

and the salts thereof formed with pharmaceutically acceptable bases, wherein X is methyl.

2. A method of claim 1 wherein X is p-methyl, said compound being 1-(α-methyl phenethyl)-3-(tolylsulfonyl) urea.

3. A method of claim 1 wherein X is p-methyl, said compound being d-1-methyl-1-(α-methyl phenethyl)-3-(p-tolylsulfonyl) urea.

4. A method for the treatment of cardiac arrhythmia which comprises administering a therapeutically effective quantity of a compound of the formula:

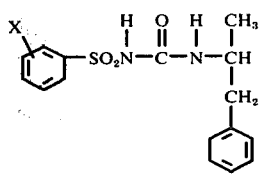

and salts thereof formed with pharmaceutically acceptable bases, wherein X is methyl.

5. A method of claim 4 wherein X is p-methyl, said compound being d-1-methyl-1-(α-methyl phenethyl)-3-(p-tolylsulfonyl) urea.

6. A method of claim 4 wherein X is p-methyl, said compound being 1-(α-methyl phenethyl)-3-(tolylsulfonyl) urea.

7. A method for the prevention of the loss of glutamic oxalotransaminase enzyme activity in cardiac tissue which comprises administering a therapeutically effective quantity of the compound of the formula:

and the salts thereof formed with pharmaceutically acceptable bases, wherein X is methyl.

8. A method of claim 7 wherein X is p-methyl, said compound being 1-(α-methyl phenethyl)-3-(tolylsulfonyl) urea.

* * * * *